United States Patent [19] [11] 4,294,684
Serwer [45] Oct. 13, 1981

[54] TEMPLATE FOR FORMING MULTIPLE GEL TRACKS WITHIN A SINGLE ELECTROPHORETIC GEL FRAME

[75] Inventor: Philip Serwer, San Antonio, Tex.

[73] Assignee: Board of Reagents, University of Texas, Austin, Tex.

[21] Appl. No.: 164,274

[22] Filed: Jun. 30, 1980

[51] Int. Cl.³ .............................................. G01N 27/28
[52] U.S. Cl. ............................ 204/299 R; 204/180 G; 204/180 S
[58] Field of Search .......... 204/180 G, 180 S, 299 R; 91/62.5

[56] References Cited

U.S. PATENT DOCUMENTS

| | | | |
|---|---|---|---|
| 2,147,458 | 2/1939 | Rohland | 91/62.5 |
| 3,495,446 | 2/1970 | Williamson | 204/180 G X |
| 3,616,387 | 10/1971 | Siebert et al. | 204/180 G |
| 3,888,759 | 6/1975 | Elson et al. | 204/299 |
| 4,061,561 | 12/1977 | Fletcher et al. | 204/180 G X |
| 4,136,007 | 1/1979 | Fujimori | 204/180 G X |
| 4,199,428 | 4/1980 | Hayashi et al. | 204/180 G X |

OTHER PUBLICATIONS

Serner et al., "Electrophoresis of Bacteriophage T7 and T7 Capsids in Agarose Gels", 28 *Jrnl. of Virology*, 917-928, (1978), Focus, vol. 1, No. 4, May/Jun. 1978.
Fangman, "Separation of Very Large DNA Molecules by Gel Electrophoresis," 5 *Nucleic Acids Research*, 653-665, (1978).
Johnson et al., "Electrophoresis of DNA in Agarose Gels," 16 *Biochemistry*, 4217-4224, (1977).
Ghosh et al., "Agarose Gel Electrophoresis of Serum Lipoproteins," 50 *Anal. Biochem.*, 592-602, (1972).

*Primary Examiner*—Arthur C. Prescott
*Attorney, Agent, or Firm*—Arnold, White & Durkee

[57] ABSTRACT

A template and method for using the same to form multiple concentration running gel tracks within a single electrophoretic gel bed. A template body comprises a support frame maintaining in parallel alignment a set of elongate bars. A sample well forming comb is provided for use in conjunction with the template body, said comb comprising a set of teeth projecting from a base and aligned in the same fashion as the elongate bars. The template body and comb are positioned in a gel bed with the well comb forming the electrophoretic origin and the bars forming tracts running parallel with the eventual current. A liquified gel is poured into the gel bed being excluded by the template in part, thereby forming the eventual gel running tracts and sample wells. After the gel hardens the template body is removed and the gel running tracks are filled with varying concentrations of gels. After the running gels have hardened the sample well forming comb is removed to allow introduction of a sample for subsquent electrophoresis.

9 Claims, 5 Drawing Figures

TEMPLATE FOR FORMING MULTIPLE GEL TRACKS WITHIN A SINGLE ELECTROPHORETIC GEL FRAME

BACKGROUND OF THE INVENTION

The present invention relates to template devices and more particularly, the invention relates to a template for forming multiple-concentration gel tracks in an electrophoretic gel bed.

Gel electrophoresis is a technique that is currently used in the separation of proteins, lipoproteins and DNA. More recently this technique has been demonstrated to be useful in the separation and characterization of bacteriophages, [Serwer, P. and Pichler, M. E., Electrophoresis of Bacteriophage T7 and T7 Capsids in Agarose Gels, 28 *Journal of Virology* 917 (1980)]. Electrophoretic mobilities in agarose gels are determined by average electrical surface charge density ($p$) and particle size. Assuming particles to be spherical, the mobility in the absence of a gel is more dependent on $p$ than size [Shaw, *Electrophoresis*, Academic Press (1969)]. Therefore, particles of similar charge but different radius are not separated in the absence of a gel. To accentuate the size differential of particles, electrophoresis is conducted in agarose gels of varying concentrations. As the concentration of agarose is increased the mobility of particles decreases during electrophoresis. Furthermore, the mobilities of the larger particles decrease more than mobilities of smaller particles. This is called differential sieving. It is this differential sieving which induces the fractionation and separation of a mixture of particles of equals $p$, such as DNA or some protein, into discrete units.

On the basis that the logarithm of electrophoretic mobility is a linear function of gel concentration, the absolute electrophoretic mobility of a particle in the absence of agarose can be determined by extrapolating the log (mobility) versus agarose concentration line to 0% agarose. The slope of the plot of mobility against gel concentration can also be used to help determine the size of particles. A problem the experimenter faces is increasing the accuracy of these extrapolations by using techniques that minimize variations in temperature and voltage gradients among the gels and prevent shrinkage of gels during electrophoresis. While extrapolation to a theoretical value becomes more accurate as the concentration of agarose is decreased, the practical aspects of gel electrophoresis become increasingly more difficult. As the agarose concentration is decreased the gels become increasingly fragile and, therefore, difficult to load and to stain for visualization.

Various procedures heretofore have been employed to develop a more precise electrophoretic mobility versus gel concentration pattern. For example, the FANGMAN BOX sold by Bethesda Research Laboratories is used to encase a single running gel within a higher concentration of agarose frame gel. The purpose of the frame gel is to provide structural stability to the less viscous running gel. Low concentration running gels on the order of 0.1% w/v or greater are routinely employed in this electrophoretic technique, thereby extending the lower limits of the experimental line on a log (mobility) versus gel concentration plot. However, as a drawback in performing the experiment, the experimenter must employ several FANGMAN BOXES each having a different concentration of running gel or sequentially perform the electrophoresis in the same box changing the gel concentration after each run. Either method introduces variable error in the experiment involving temperature, humidity, and voltage gradients which cannot be controlled or normalized from box to box or run to run.

In efforts to normalize the random error imposed by ambient conditions from batch to batch, experimenters have tried running multiple concentration gels in the same apparatus. A vertical apparatus for agarose gel electrophoresis is described by Johnson, P. H. and Grossman, L. I., 16 *Biochemistry* 4217 (1977). The apparatus consists of a vertical gel bed equipped with plastic partitions separating the gel bed into several frames, each frame of which is filled with a gel of varying agarose concentrations. A drawback to this compartmentalization system is that gel concentrations less than 0.4% are not feasible in that there is slippage of gels from between the plates holding them, sample wells break during comb removal, there is difficulty in handling the gels for staining, and there is shrinkage of the gels during electrophoresis. Although the shrinkage problem and to a limited extent the well breakage problem can be overcome by running the electrophoresis in a horizontal mode, the other problems still exist so as to offer imprecise data.

From the foregoing, it will be appreciated that those techniques which encase the running gel within a frame gel for stability do not permit the use of multiple gels, and therefore do not normalize errors induced by ambient conditions. Moreover, those techniques for running several gels in a single apparatus are limited to relatively high gel concentration ($\geq 0.4\%$ w/v) such that an accurate extrapolation to absolute electrophoretic mobility is difficult to achieve.

As a result of the shortcomings of the prior art, typified by the above, there has developed and continues to exist a substantial need for a means to develop multiple concentration gel tracks in a single gel bed which will also accommodate low concentration gels. Despite this recognized need, such a device has heretofore been unavailable.

SUMMARY OF THE INVENTION

According to the present invention, a template has been developed for embedding several running tracks within a single agarose gel frame, each track of which may accommodate a concentration of agarose running gel independently different from the other tracks. Samples placed in wells at the origin of each running gel are simultaneously subjected to electrophoresis.

The present invention is summarized in that a template for forming multiple concentration gel running tracks in a single gel frame includes a support frame maintaining in parallel alignment a set of rigid elongate bars which serve to exclude poured frame gel from the eventual running tracks. The elongate bars of the preferred embodiment desirably have a substantially rectangular cross-section, although other geometric shapes can also be employed. Further, the template includes a sample-well forming comb used in conjunction with the template body, centering the sample wells on the anode head of the running tracks. The sample wells serve as the gel electrophoretic origin for sample introduction onto the running tracks.

Additional features of the preferred template embodiment include bars with tapered sides to facilitate removal of the device from the frame gel after the gel has hardened, bars constructed or coated with a nonadhering surface such as TEFLON to prevent adhesion of the gel frame to the template, and a handgrip coupled to the support frame to facilitate manipulation of the template.

Further in accordance with the present invention, a method of using the described template is disclosed for preparing a multigel consisting of several agarose running gel tracks embedded within a surrounding frame gel, wherein the concentrations of agarose in each of the running gel tracks and in the frame gel can be varied independently of one another. The method includes providing an electrophoretic gel tank having a gel bed which will accommodate the described template; placing the template body with the elongate bars in contact with the gel bed floor; positioning the template body in the bed such that the bars run longitudinally with the direction of the eventual electrical current; disposing the sample-well forming comb at one end of the template body; pouring liquified agarose into the gel bed; allowing the agarose to harden thereby forming a gel frame; removing the template body; filling the running tracks with desired concentrations of agarose; and removing the sample well forming comb for subsequent introduction of the sample.

From the foregoing, it will be appreciated that the described invention features the capacity for forming multiple concentration gel tracks within a single gel frame. As a result of incorporating all of the running gels used for electrophoresis within a single bed, fluctuations in temperature and voltage gradients occur in all gels simultaneously. Therefore, errors resulting from inability to obviate temperature or field gradients are normalized among the several running tracks of a multigel. Furthermore, because the gel is subject to horizontal electrophoresis, no significant gel shrinkage occurs. Moreover, by providing support for the running gels with a surrounding gel frame it is possible to run electrophoresis in gels with a concentration as low as 0.03% [weight/volume (w/v)] agarose, whereas it is believed that 0.1% (w/v) is the limit without the gel support. Further, surrounding the sample wells on four of five sides with the gel frame strengthens the sample wells and greatly decreases the chance of running gel damage while loading the sample. Additionally, the frame gel provides support of the gel tracks during subsequent staining procedures.

Other features and advantages of the present invention will become apparent from the following description of the illustrative embodiment when taken in conjunction with the accompanying drawings.

BRIEF DESCRIPTION OF THE DRAWINGS

A more complete appreciation of the invention may be had by reference to the accompanying drawings, which illustrate a preferred embodiment of the invention to be described in detail, wherein.

DETAILED DESCRIPTION OF THE ILLUSTRATIVE EMBODIMENT

Figure 1:
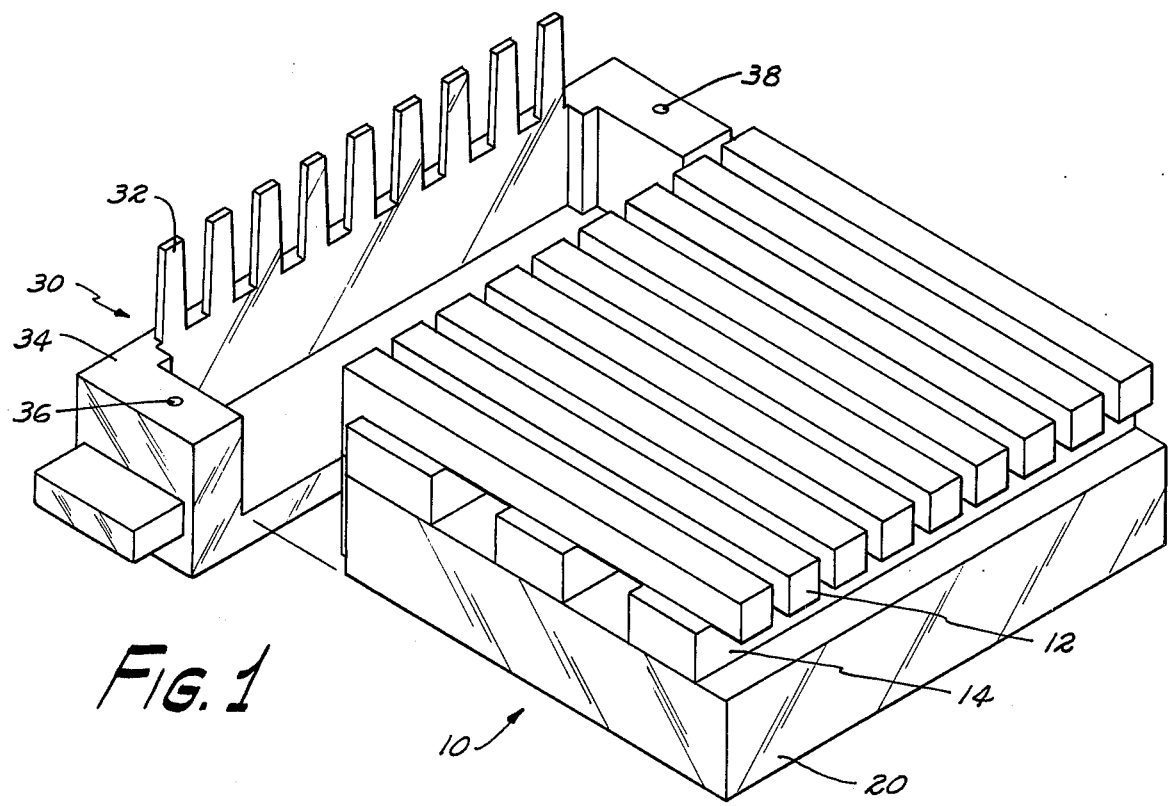
FIG. 1 is a perspective view of an embodiment of the template for forming multiple concentration running gel tracks within an electrophoretic gel bed.

Referring now to the drawings, and particularly to FIG. 1, there is illustrated a template for forming multiple concentration gel tracks in a gel bed. The template includes a template body 10 comprising a plurality of rigid elongate bars 12 each of which is securely attached to a support frame 14 in a parallel alignment with respect to the other bars. Further, a handgrip 20 may be attached to the free surface of the support frame 14 to facilitate the manipulation of the template in forming the gel tracks. Although it may be desirable to include a handgrip, it is not a necessary element to the proper functioning of the structure. In addition, the template encompasses the use of a sample-well forming comb 30 which is used in cooperation with the template body 10 to impress the sample origin for the gel electrophoretic process.

In particular, FIG. 1 illustrates a preferred embodiment of the invention. Template body 10 further includes a plurality of rigid elongate bars 12 shown in the embodiment as substantially rectangularly cross-sectioned pieces. Elongate bars 12 are desirably formed of an inert, smooth surfaced material, preferably TEFLON although any other equivalent material may be suitable so as to impart an impression in a gel mold without reacting with the gel and without adhering to the gel as the template is removed. Each elongate bar 12 is securely attached to a support frame 14 in a parallel alignment with respect to the other bars. As shown in FIG. 1, template body 10 provides nine parallel bars such that nine parallel running tracks will be molded in a gel frame. The number of parallel bars of course may be varied more or less depending on the number of gel tracks that are desired, and be accommodated by a gel bed. The bars 12 may be attached to the support frame by any secured fashion, such as screws, bolts, epoxy, or adhesive glue. In particular, the illustrative embodiment featured in FIG. 1 comprises the support frame 14 and nine parallel bars as an integral unit. More particularly, the template body 10 in FIG. 1 was milled from a TEFLON block. First the support frame 14 composed of three parallel rectangularly cross-sectioned cross-pieces is machined into a TEFLON block. Second, an acrylic plastic handgrip 20, such as PLEXIGLAS, is affixed to the support frame 14 imparting additional rigid support to the somewhat flexible TEFLON support frame 14. Attachment of the handgrip 20 to support frame 14 is desirably accomplished with screws anchored in the plastic handgrip 20 and threaded into the support frame 14. Finally, the elongate bars 12 are milled in parallel alignment, each bar 12 equidistant from an adjacent bar 12. Alternatively, the TEFLON block may first be affixed to the handgrip without milling a frame of cross-pieces and then the elongate bars may be milled into the free surface of the block.

As further shown in FIG. 1, there is a sample-well forming comb 30 having a plurality of rigid teeth 32 projecting linearly from a base 34. As featured in FIG. 1, the number of teeth 32 mounted on the base 34 of the comb corresponds to the number of elongate bars 12 provided by the template body 10. In addition, each tooth 32 is positioned along the base 34 the same distance from each other as exists between the elongate bars 12. The sample well forming comb 30 and template body 10 interlock and are used in cooperation with each other in forming multiple concentration gel running tracks in a gel bed and corresponding origin sample wells, centered at the anode head of the running tracks.

Figure 2:
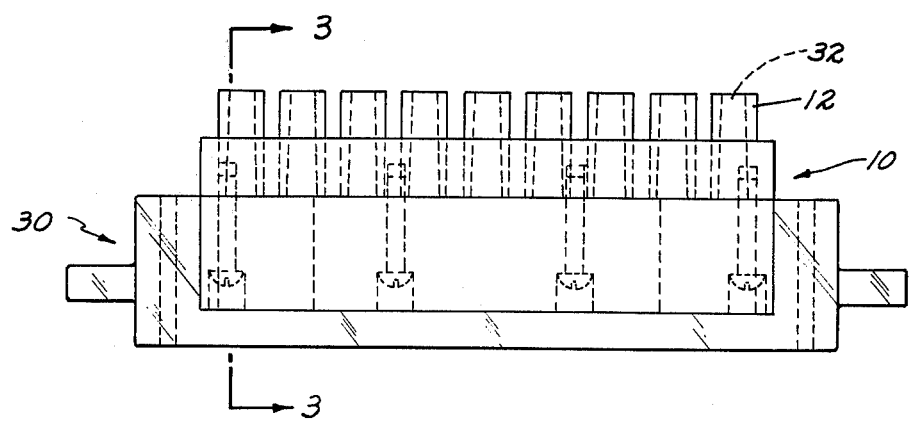
FIG. 2 is an end view of the template with the sample-well forming comb in place at the distal end of the template body.

Referring next to FIG. 2, an end view of the template is shown with the sample-well forming comb 30 in place at the distal end of template body 10. This view features the shape and spacing of elongate bars 12. In accordance with the preferred embodiment, each bar has substantially a rectangular cross-section with slight tapering of the sides about 1.5° off vertical. Tapering the sides of bars 12 facilitates pulling of the template body from the gel mold without disturbing the impressed configuration of the gel tracks. The depth and width of the elongate bars 12 are preferably on the order of 0.4 inch, respectively, although dimensions may vary widely depending on the size of gel tracks that is desired and the capacity of the gel bed. Furthermore, the distance between two adjacent bars 12 is also variable depending on the capacity of the gel bed. The illustrative preferred embodiment has approximately 0.16 inch spacing between each of the nine bars 12, each bar 12 of which is approximately 0.4 inch wide and deep. A template body 10 of these dimensions will readily be accommodated by commercially available gel beds.

Figure 3:
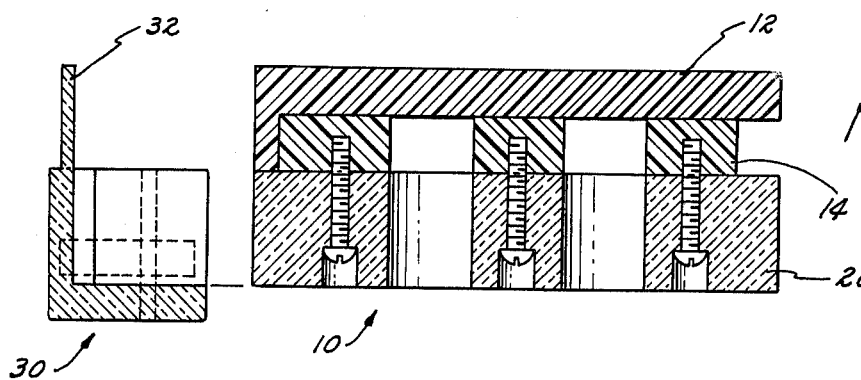
FIG. 3 is a cross sectional side view taken along line 3—3 of FIG. 2.

Turning now to FIG. 3, there is depicted a cross-sectional side view of the template body 10 disposed relative to sample-well forming comb 30. Here it is shown that each bar 12 is mounted onto the cross pieces of frame 14. Further, handgrip 20 is anchored to the opposite surface of support frame 14. This particular cross sectional view features a cutout in the handgrip 20 for insertion of the fingers.

Figure 4:
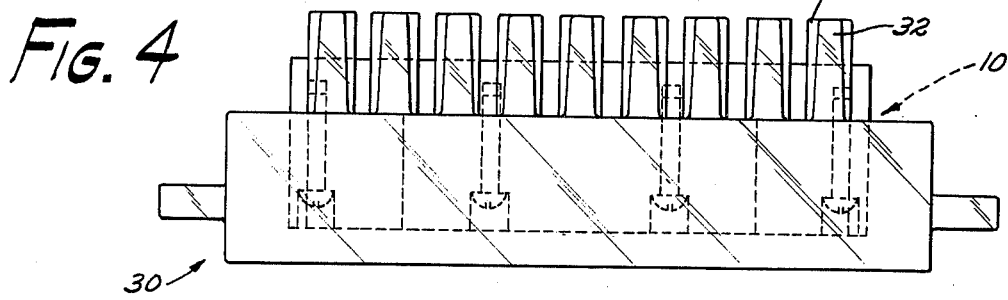
FIG. 4 is an end view of the template with the sample-well forming comb in place at the proximal end of the template body.

Referring now to FIG. 4, an end view of template body 10 and sample-well forming comb 30 is presented. Comb 30 is detachably disposed relative to the proximal end of template body 10 such that each tooth 32 is directly aligned with and abutting an end of an elongate bar 12. In the illustrated preferred embodiment, each tooth 32 substantially overlaps the end of a bar 12. Moreover, each tooth 32 of the illustrative embodiment as tapered so as to facilitate withdrawal of the comb 30 from a molded gel.

Figure 5:
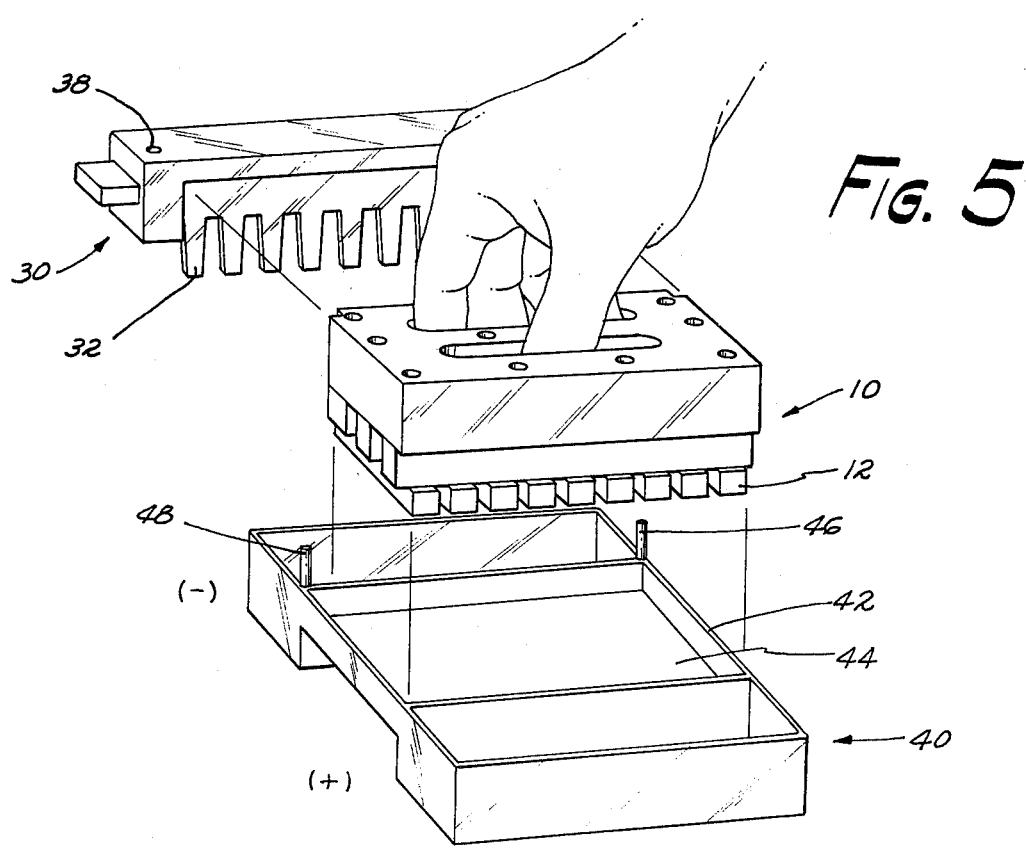
FIG. 5 is a perspective view of the template oriented in association with a gel electrophoresis tank.

With a template in accordance with the present invention, formation of multiple concentration running tracks in a gel bed will expedite gel electrophoretic characterization and separation of large molecules and viral material. In such a method as illustrated in FIG. 5, a commercially available gel tank 40 such as that designed by Dr. F. W. Studier and obtained from Aquebogue Machine and Repair Shop, Aquebogue, N.Y., is provided for the foundation of the eventual running tracks. In FIG. 5, template body 10 is positioned within a gel bed 42 having the elongate bars addressed longitudinally within the gel bed and parallel with the eventual electrophoretic current path. After the template body 10 is in place, the sample-well forming comb 30 is lowered into the anode (−) end of the gel bed 50 having the teeth 32 projecting perpendicular to and about 1 mm from the gel bed floor 44. In the preferred embodiment each end of comb 30 has a vertical bore 36, 38 (refer back also to FIG. 1 for reference number 36) which accepts for positioning, guide pins 46, 48 respectively, each pin projecting vertically from one to two adjacent corners of gel bed 42. The pins prevent vibration-induced damage to running gels during removal of the comb 30. The sample-well forming comb 30 and template body 10 interlock within the gel bed 42 such that the teeth 32 of comb 30 are aligned flush with one set of ends formed by elongate bars 12. Next liquified agarose gel, conventionally a 1.5% w/v agarose gel, is poured into the gel bed 42. Agarose is excluded from the eventual running tracks by the template. Aftr allowing the agarose frame gel to harden for 30–35 minutes, the template body 10 and comb 30 are removed from the agarose frame gel by slowly pulling in a vertical direction using the handgrip 20 or the support frame 14 if there is no handgrip. Removal of the template body exposes a plurality of running tracks. The bottoms of the tracks produced by the bars 12 are cleaned. Further, comb 30 is replaced in its original position within the gel bed. The tracks formed in the frame gel are filled individually with varying concentrations of agarose. The concentrations of the running gels may desirably vary from 0.03 to 1.5% (w/v) agarose. The running gels are allowed to harden for 30–35 minutes at room temperature. The gel tank 40 is prepared for electrophoresis in the conventional manner including filling buffer tanks with the appropriate buffer. The comb 30 is slowly removed and samples are loaded into the sample wells formed by the teeth of the sample-well forming comb. The sample-well forms the origin of the electrophoretic process at the anode terminus of the running tracks gel. Electrophoresis is then performed in the conventional manner as further described in applicant's paper, Serwer, P., A Technique for Electrophoresis in Multiple-Concentration Agarose Gels, 101, *Analytical Biochemistry* 154 (1980).

From the foregoing detailed description, it will be appreciated that the present invention provides an accurate, economical and time-saving technique for performing gel electrophetic characterization and separation of particles. Furthermore, by incorporating all of the gels used for electrophoresis within a single gel frame, differences in temperature and voltage gradients occur in all the gels simultaneously thereby normalizing these parameters with respect to a single experiment.

The foregoing description of the invention has been directed to a particular preferred embodiment for purposes of explanation and illustration. However, it will be apparent to those skilled in the art that a template for forming multiple concentration running gel tracks may take on other forms.

What is claimed is:

1. A template for forming multiple gel tracks in a gel bed, which comprises:
   a support frame;
   a plurality of rigid elongate bars, each bar spaced a sufficient distance from an adjacent bar effective to form gel tracks in a gel bed, each bar of which is securely attached to the support frame in a parallel alignment with respect to the other bars; and
   a sample-well forming comb having a plurality of teeth projecting linearly from a base, said comb adapted to be detachably disposed with respect to the support frame, the teeth of the comb aligned in a manner to form a flush contact with one set of ends presented by the elongate bars.

2. The template of claim 1 wherein:
   each bar is spaced equidistant from an adjacent bar.

3. The template of claim 1 wherein:
   the elongate bars comprise a length of rigid material having a nonadhering surface.

4. The template of claim 1 wherein:

...ne elongate bars are substantially rectangular in cross-section.

5. The template of claim 1 wherein:
the support frame and elongate bars form an integral unit.

6. The template of claim 1 wherein:
the base of the sample-well forming comb has a bore running vertically through each end of the base, each bore being adapted for accommodating a guide pin projecting from a gel bed.

7. The template of claim 1 wherein:
the teeth of the sample-well forming comb are tapered.

8. The template of claim 1 which further comprises:
a handgrip structure mounted to the surface of the support frame.

9. A method of forming multiple running gel tracks within a single solidified gel frame employing a template which includes a sample-well forming comb and template body presenting a plurality of elongate bars in parallel alignment, said method comprising the steps of:

providing an electrophoresis gel tank having a gel bed formed therein;

positioning the template body within the gel bed, having the elongate bars addressed longitudinally within the gel bed and parallel with the eventual electrophoretic current path;

lowering the sample-well forming comb into the anode end of the gel bed, having the teeth of said comb projecting perpendicular to the floor bed and aligned flush with a set of ends formed by the elongate bars;

pouring liquified gel into the gel bed, wherein the gel is excluded by the template thereby forming the eventual gel running tracks and sample well origins impressed into a solidified gel frame;

removing the template body from the gel bed after solidification of the surrounding gel while retaining the sample-well forming comb in position thereby exposing a plurality of mold running tracks impressed in a solidified gel frame;

filling each running track with a dilute concentration of gel.

* * * * *

UNITED STATES PATENT OFFICE
CERTIFICATE OF CORRECTION

Patent No. 4,294,684                    Dated October 13, 1981

Inventor(s) Phillip Serwer

It is certified that error appears in the above-identified patent and that said Letters Patent are hereby corrected as shown below:

Assignee, "Reagents" should read --Regents--.

Other Publications, line 1, "Serner" should read --Serwer--.

In the Abstract, lines 11 and 14, "tracts" should read
    --tracks--.

Column 1, lines 19 and 21, "$\rho$" should read --$\sigma$--;
    and line 33, "equals $\rho$" should read --equal $\sigma$--.

Column 4, line 38, "and be" should read --and can be--.

Column 5, line 43, "as" should be --is--; and
    line 65, "one to two" should read --one of two--.

Column 6, line 6, "Aftr" should read --After--; and
    line 36, "electrophetic" should read --electrophoretic--.

Signed and Sealed this

Nineteenth Day of January 1982

[SEAL]

Attest:

GERALD J. MOSSINGHOFF

Attesting Officer    Commissioner of Patents and Trademarks